United States Patent [19]
Nakamura et al.

[11] Patent Number: 5,745,163
[45] Date of Patent: Apr. 28, 1998

[54] OCULAR FUNDUS CAMERA

[75] Inventors: Toshihisa Nakamura; Tomohiko Hattori, both of Nakai-machi, Japan

[73] Assignee: Terumo Kabushiki Kaisha, Tokyo, Japan

[21] Appl. No.: 893,188

[22] Filed: Jul. 15, 1997

Related U.S. Application Data

[63] Continuation of Ser. No. 572,022, Dec. 14, 1995.

[30] Foreign Application Priority Data

| Dec. 16, 1994 | [JP] | Japan | 6-313740 |
| Sep. 20, 1995 | [JP] | Japan | 7-242194 |
| Sep. 20, 1995 | [JP] | Japan | 7-266378 |

[51] Int. Cl.$^6$ ............. A61B 3/14; H04N 7/18; H04N 13/02
[52] U.S. Cl. ............. 348/46; 348/71; 351/206
[58] Field of Search ............. 348/42, 45, 46, 348/78; 351/206; 382/117; H04N 7/18, 13/02

[56] References Cited

U.S. PATENT DOCUMENTS

| 4,111,695 | 9/1978 | Yevick | 430/494 |
| 4,159,163 | 6/1979 | Dudley | 359/478 |
| 4,370,033 | 1/1983 | Kani | 351/206 |
| 4,761,066 | 8/1988 | Carter | 359/371 |
| 4,786,155 | 11/1988 | Fantone et al. | 356/39 |
| 4,933,756 | 6/1990 | Sekine | 348/78 |
| 5,140,352 | 8/1992 | Moore | 348/78 |
| 5,557,321 | 9/1996 | Kohayakawa | 348/78 |
| 5,615,278 | 3/1997 | Matsumoto | 382/128 |

FOREIGN PATENT DOCUMENTS

| 0 230 253 A2 | 7/1987 | European Pat. Off. |
| 28 47 962 | 5/1979 | Germany |
| 30 06 373 | 9/1980 | Germany |
| 33 27 672 A1 | 2/1985 | Germany |
| 54-066854 | 5/1979 | Japan |

*Primary Examiner*—Howard W. Britton
*Attorney, Agent, or Firm*—Burns, Doane, Swecker & Mathis, LLP

[57] ABSTRACT

An ocular fundus camera apparatus includes an ocular fundus camera having an optical lens that transfers first and second image light components which have a parallax therebetween and which can be separated from each other, a memory for storing a predetermined coefficient a based on the shape of the optical lens, and a CCD for converting the first and second image light components into first and second image signals (A, B). The ocular fundus camera apparatus generates first and second image data (L, R) by performing proportional distribution of the first and second image signals in accordance with the predetermined coefficient.

36 Claims, 18 Drawing Sheets

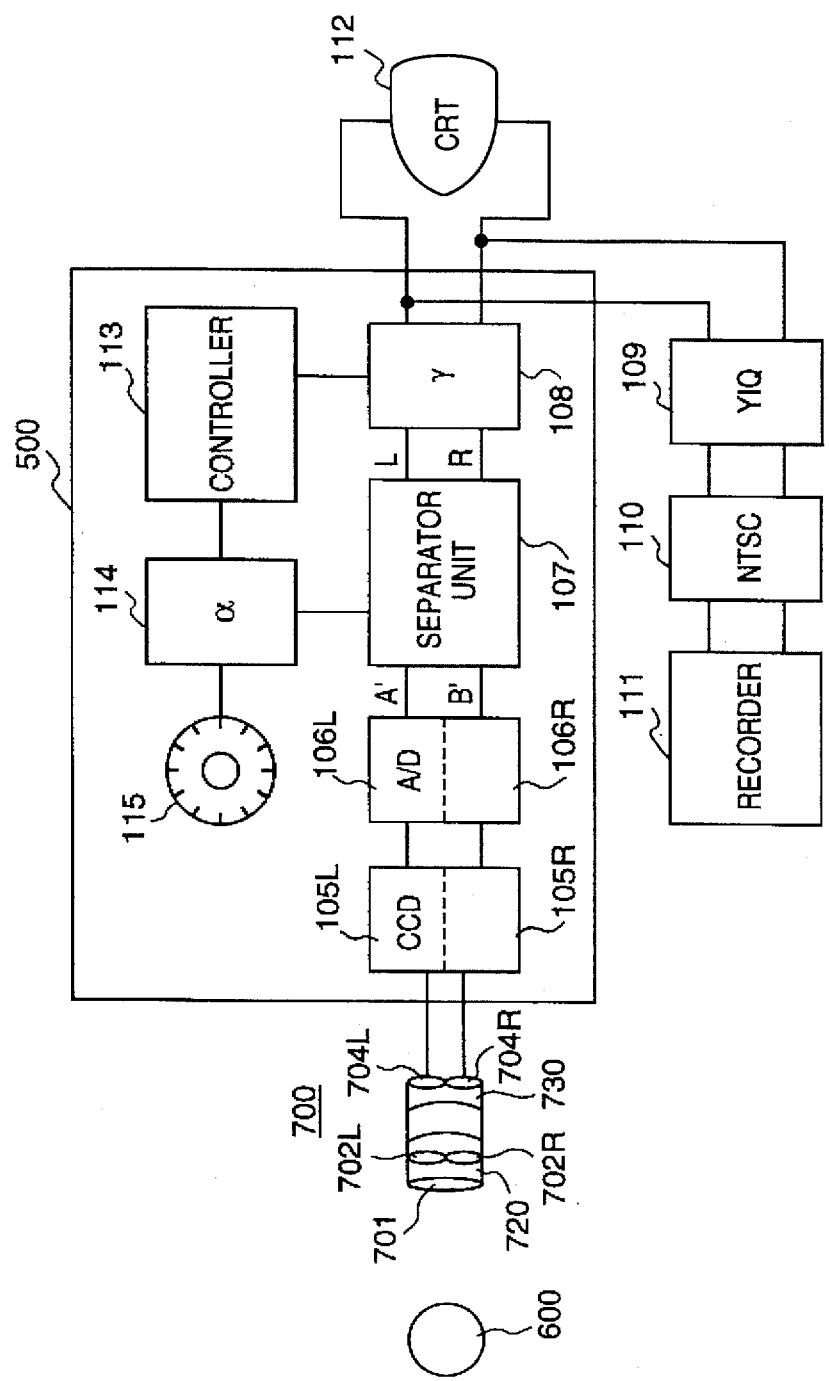

ROTATION OF PLANE OF POLARIZATION

OCULAR FUNDUS CAMERA

This application is a continuation of application Ser. No. 08/572,022, filed Dec. 14, 1995.

BACKGROUND OF THE INVENTION

The present invention relates to an ocular fundus camera allowing stereoscopic observation.

An optical ocular fundus camera transfers an enlarged image to the eyes of an observer or a visual display apparatus through an appropriate combination of an eyepiece and an objective lens. However, it is difficult to obtain information on the depth of a fundus portion from an image sent from the optical ocular fundus camera having a single objective lens.

There is provided a stereoscopic optical apparatus in which two parallax images are received by two objective lenses and transferred to the right and left eyes of the observer through two image transfer optical systems, so that the observation image becomes stereoscopic. However, as this stereoscopic optical apparatus requires a plurality of optical systems, its structure is complicated, leading to a high cost.

SUMMARY OF THE INVENTION

The present invention has been made in view of the above problems.

An object according to the present invention is to provide an ocular fundus camera is capable of transmitting stereoscopic images using a single optical system.

Another object of the present invention is to provide an image processing apparatus for an ocular fundus camera that can generate image data from two image light components whose polarized states have been changed as they are transferred through one optical system, based on image light whose polarized state has not been changed.

In order to achieve this object, according to the present invention, there is provided an image processing apparatus for an ocular fundus camera having an optical system that transfers first and second image light components which have a parallax therebetween and which can be separated from each other, comprising:

converting means for converting the first and second image light components into first and second image signals, and generating means for generating first and second image data by performing proportional distribution of the first and second image signals in accordance with a predetermined coefficient.

A change in polarized states of two polarized light components which pass through the optical system occurs when the plane of polarization of one polarized light component shifts, and this polarized light component becomes the other polarized light component. This change in polarized state is mainly determined by the material and shape (e.g., the number of optical systems) of the optical system. When a predetermined coefficient is determined in advance, and the first and second image data are generated by performing proportional distribution of the first and second image signals (usually electrical signals output from an image sensing element, e.g., a CCD) in accordance with the predetermined coefficient, these image data exhibit values close to those of image data obtained from image signals that are obtained from image light components whose polarized states probably do not change. Accordingly, when this image processing apparatus is used, a complicated, expensive optical system which holds a plane of polarization, need not be employed in the ocular fundus camera.

It is another object of the present invention to provide an ocular fundus camera apparatus which can separate at high precision two polarized images sent from an ocular fundus camera having one optical system that allows a change in polarized state of image light upon transfer.

In order to achieve this object, according to the present invention, there is provided an ocular fundus camera apparatus comprising:

an ocular fundus camera having an optical system that transfers first and second image light components which have a parallax therebetween and which can be separated from each other, converting means for converting the first and second image light components into first and second image signals, and generating means for generating first and second image data by performing proportional distribution of the first and second image signals in accordance with a predetermined coefficient.

More specifically, this ocular fundus camera apparatus can provide a system that does not require an optical system for holding a plane of polarization and that can generate two image data, which are separated from each other at high precision, from two image light components (having planes of polarization shifted from each other) sent from an ocular fundus camera having an inexpensive optical system.

It is still another object of the present invention to provide an ocular fundus camera controlling method that enables high-precision separation of two polarized images sent from an ocular fundus camera using an inexpensive optical system.

In order to achieve this object, according to the present invention, there is provided a method of controlling an ocular fundus camera having an optical system that transfers first and second image light components which have a parallax therebetween and which can be separated from each other, comprising the steps of converting the first and second image light components into first and second image signals by controlling an image sensing element, and generating first and second image data by performing proportional distribution of the first and second image signals based on conversion characteristics of the image sensing element and a predetermined coefficient.

With this controlling method, although the two image light components obtained by an ocular fundus camera, that does not require an optical system for holding a plane of polarization and that has an inexpensive optical system, have planes of polarization that are shifted from each other, two image data can be generated in which the two image light components are separated from each other at high precision.

According to an aspect of the present invention, the predetermined coefficient is determined in advance based on a material, count, and shape of a lens provided to the optical system. These factors control the change amounts of the polarized states of two polarized light components in the optical system. With this coefficient, the change ratios of the polarized states can be quantified.

According to another aspect of the present invention, the image processing apparatus further comprises means for inputting the material, shape, and count of the lens. The operability in an operation for obtaining stereoscopic images can be improved.

According to still another aspect of the present invention, the image processing apparatus further comprises adjusting means, allowing a user to operate, for adjusting the coefficient. The operability in an operation for obtaining stereoscopic images can be improved.

According to still another aspect of the present invention, the converting means has an image sensing element (e.g., a CCD) for converting the first and second image light components into the first and second image signals as electrical signals, and inverting means for inverting the first and second image signals sent from the image sensing element into first and second light intensity data representing light intensities. As an output (usually an electrical signal) from the image sensing element is not linearly related to the intensity of the incident light, high-precision proportional distribution cannot be executed by directly using the first and second image signals. However, when the first and second image signals are inverted into the first and second light intensity data representing the light intensities, proportional distribution can be performed in accordance with the predetermined coefficient.

According to still another aspect of the present invention, the first and second image light components in the optical system are polarized substantially differently from each other.

According to still another aspect of the present invention, the first and second image data are stored or displayed for the convenience of later use, thereby improving the practicality.

The image processing apparatus and the controlling method of the present invention can be applied to various types of ocular fundus cameras.

For example, according to still another aspect of the present invention, the optical system of the ocular fundus camera has an incident portion provided to a distal end side of the ocular fundus camera, and an exit portion provided to a proximal end side of the ocular fundus camera, and the incident portion has a pair of polarization filters which are provided at an effective center serving as an aperture in a direction of an optical axis or in a vicinity thereof, which have different polarization azimuths, and which are divisionally disposed on right and left regions of a plane substantially perpendicular to the optical axis. In this ocular fundus camera, two polarization filters can be appropriately arranged in one barrel. Accordingly, the pair of polarization filters in this ocular fundus camera have semicircular shapes.

For example, according to still another aspect of the present invention, the optical system of the ocular fundus camera has an incident portion provided to a distal end side of the ocular fundus camera, and an exit portion provided to a proximal end side of the ocular fundus camera, and the exit portion has polarization axis rotating means for rotating polarization axes of two polarized images passing through the ocular fundus camera in a time-interlace manner, and an analyzer provided behind the rotating means.

With this ocular fundus camera, although the obtained images are divided in the time-interlace manner, the arrangement of the exit portion is simplified.

For example, according to still another aspect of the present invention, the optical system of the ocular fundus camera has an incident portion provided to a distal end side of the ocular fundus camera, and an exit portion provided to a proximal end side of the ocular fundus camera, and the exit portion has a beam splitter for separating optical paths of two polarized images passing through the ocular fundus camera, and a pair of polarization filters respectively passing the separated polarized images therethrough and having polarization azimuths different from each other.

With this ocular fundus camera, two time-parallel image data can be obtained.

It is still another object of the present invention to provide an objective adapter for an ocular fundus camera that is suitable for the above ocular fundus camera apparatus and can adjust the angle of plane of polarization in the barrel.

In order to achieve this object, according to the present invention, there is provided an objective adapter of an ocular fundus camera having an objective lens in a barrel thereof, comprising a pair of polarization filters arranged side by side at an effective center serving as an aperture of the objective lens in a direction of a plane perpendicular to an optical axis of the barrel, and means for rotating the pair of polarization filters about the optical axis in the barrel as a center.

According to still another aspect of the present invention, the barrel has a first barrel portion for supporting at least the pair of polarization filters and a second barrel portion for supporting a remaining portion of the adapter, the first barrel portion being supported to be pivotal with respect to the second barrel portion, and at least one of the first and second barrel portions is formed with a scale for aiding visual observation of a pivot amount of the first barrel portion.

According to still another aspect of the present invention, the pair of polarization filters have semicircular shapes and substantially form a circle when fitted with each other.

It is still another object of the present invention to provide a stereoscopic ocular fundus camera which converts two polarized images into two parallax images and transfers them as right- and left-eye images, wherein even when incident light itself to an observation lens has polarizing characteristics, a high-quality stereoscopic image can be obtained.

The present invention has been made in view of the above problem, and has as its object to provide an ocular fundus camera which enables high-quality stereoscopic observation by solving the nonuniformity in polarized state existing in the incident light.

In order to achieve the above object, there is provided an ocular fundus camera for separating image light incident through an observation lens into two polarization images, propagating the two polarization images through one optical path, and using the two polarized images as two parallax images, comprising equalizing means, provided in front of the observation lens, for equalizing two polarized light components of incident light, and optical means for separating the incident light having two equalized polarized light components, whereby intensities of the two parallax images obtained by the optical means become equal.

According to still another aspect of the present invention, the equalizing means is made of a material having such optical characteristics that it solves polarization characteristics of the incident light.

According to still another aspect of the present invention, the equalizing means has means, e.g., a phase shifter, for rotating the polarization azimuth of the incident light.

According to still another aspect of the present invention, the equalizing means has a phase shifter and a light-transmitting plate which have equal areas, and said optical means comprises a pair of polarization filters having polarization azimuth different from each other and having a same area. An area of said phase shifter is a same as that of said of said light-transmitting plate, and the pair of polarization filters have a same area, whereby light which is phase-shifted by said phase shifter and light which passes said light-transmitting plate are incident on said pair of polarization filters. Thus, the light beams which emerge from the pair of filters have an identical intensity.

According to another aspect of the present invention, the phase shifter and light-transmitting plate may be a plurality of pieces.

According to another aspect of the present invention, the phase shifter shifts a phase of transmitting light by λ/2.

According to another aspect of the present invention, a primary surface of said pair of polarization filters is perpendicular to an optical axis of the camera, and a primary surface of said phase shifter and light-transmitting plate is perpendicular to the optical axis of the camera.

According to another aspect of the present invention, primary surfaces of the pair of polarization filters are substantially semicircular, and are flush with each other to make a circle, and said primary surfaces of the said phase shifter and light-transmitting plate are substantially semicircular, and are flush with each other to make a circle.

According to another aspect of the present invention, a first line which separates one of said pair of polarization filters from the other of said pair of polarization filters is perpendicular to a line which separates said phase shifter from said light-transmitting plate.

According to another aspect of the present invention, a first line which separates one of said pair of polarization filters from the other of said pair of polarization filters is parallel to a line which separates said phase shifter from said light-transmitting plate.

Other feature and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 2 shows the arrangement of an ocular fundus camera apparatus (ocular fundus camera system) according to the first embodiment of the present invention;

DETAILED DESCRIPTION OF THE PREFERRED EMBODIMENTS

A stereoscopic ocular fundus camera apparatus of the present invention will be described in detail with reference to the accompanying drawings.

<Overall Arrangement of Ocular Fundus Camera System>

Figure 1A:
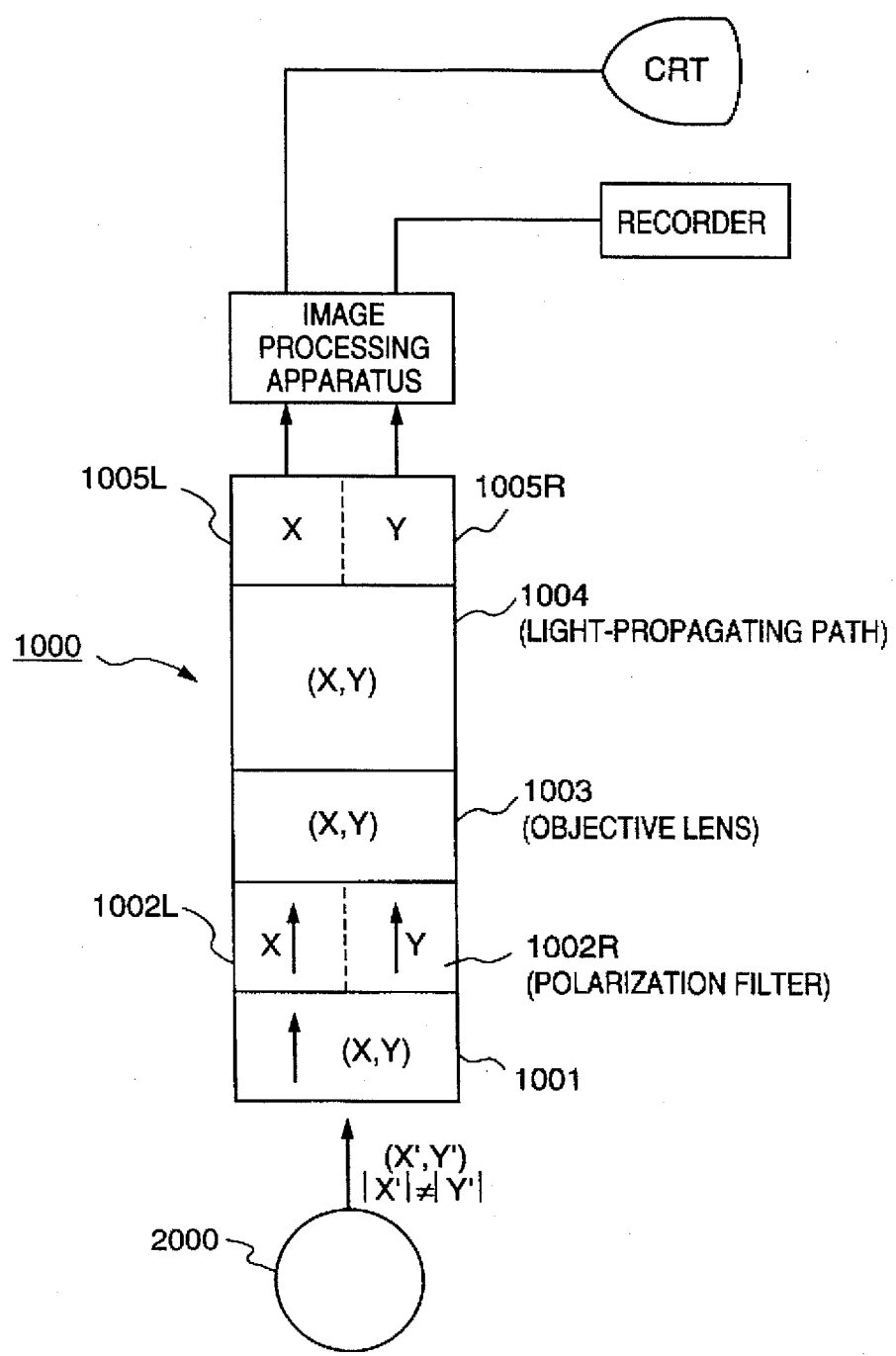
FIG. 1A is a schematic diagram showing the principle arrangement of an ocular fundus camera system as a preferable embodiment of the present invention that has a polarization intensity correcting function and a polarization shift compensating function.

FIG. 1A schematically shows the arrangement of an ocular fundus camera system having an ocular fundus camera to which the present invention is applied. In this specification, a unit which includes an optical system, e.g., an objective lens, and externally extracts the front image of an observation target object 2000 will be referred to as an "ocular fundus camera" (1000 in FIG. 1A); a unit for processing an image signal (usually an electrical signal) obtained by conversion from image light obtained by this ocular fundus camera, thereby obtaining a visual image, will be referred to as an "image processing apparatus" (500 in FIG. 1A) of the ocular fundus camera; and a system comprising the "ocular fundus camera" and the "image processing apparatus" will be referred to as an "fundus apparatus system" (or an ocular fundus camera system).

The ocular fundus camera 1000 of this embodiment has three main optical systems, i.e., a light amount equalizer unit 1001, a polarization filter unit 1002, and an objective lens 1003.

Reference numeral 2000 denotes an observation target object; and 2001, light emerging from the observation target object. Usually, the light 2001 is polarized. The light 2001 has two polarized light components. For the sake of descriptive convenience, the two polarized light components are denoted by X' and Y', and their respective polarization azimuths are denoted by X and Y. Although it suffices in principle if these polarization azimuths are different and they need not be orthogonal, for the sake of descriptive convenience, they are determined to be orthogonal and are expressed as X⊥Y. Generally, the intensities of arbitrary two polarized light components in reflected light often differ from each other. Accordingly, the intensities of the above two polarized light components X' and Y' are not also equal, which is expressed as |X'|≠|Y'| in FIG. 1A.

The light amount equalizer unit 1001 has a phase shifter, e.g., a λ/2 plate, as will be described later, and has a function of equalizing the intensities of the two polarized light components X' and Y' contained in light emerging from the observation target object 2000, in order to eliminate the non-equality of the light amounts of the two polarized light components X' and Y'. The equalized intensities are expressed as |X|=|Y|. In FIG. 1A, the two overlapping polarized light components X and Y are expressed as (X,Y) for the sake of descriptive convenience. The light amount equalizer unit 1001 transfers light containing these two polarized light components X and Y to the preceding polarization filter unit 1002.

Figure 1B:
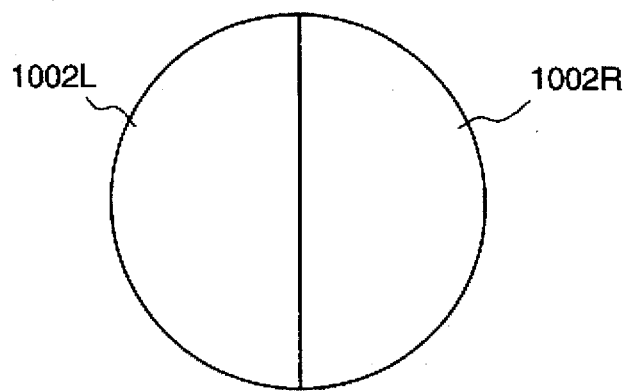
FIG. 1B shows the arrangement of a phase shifter used in the ocular fundus camera of FIG. 1A.

The polarization filter unit 1002 separates and extracts the polarized light components X and Y from the light including the overlapping polarized light components X and Y. As shown in FIG. 1B, the polarization filter unit 1002 has two filter portions 1002L and 1002R having the same area. The filter portion 1002L passes only the X-polarized light component therethrough, and the filter portion 1002R passes only the Y-polarized light component therethrough. Since the two filter portions 1002L and 1002R are separated, the polarized light component X passing through the filter portion 1002L forms an image for the observer's left eye, and the polarized light component Y passing through the filter portion 1002R forms an image for the observer's right eye.

Both the polarized light components X and Y emerging from the polarization filter unit 1002 are incident on the objective lens 1003. In the objective lens 1003, the two polarized light components X and Y overlap. This is expressed as (X,Y). The objective lens 1003 guides the two overlapping polarized light components (X,Y) to a barrel 1004. The two polarized light components (X,Y) propagate through the image guide 1004 and are guided to a photoelectric converter unit 1005. The photoelectric converter unit 1005 separates and extracts the two polarized light components and converts the separated polarized light components into electrical signals.

An image signal output from the photoelectric converter unit 1005 as the electrical signal is converted by the image processing apparatus 500 into an image signal for a CRT display unit or for a recorder.

When the two polarized light components X and Y propagate through the barrel 1004, both of their polarization azimuths are subjected to shift. Due to this shift, when the two polarized light components are incident on the photoelectric converter unit 1005, the X-polarized light component for the left-eye image becomes a Y-direction component, and the Y-polarized light component for the right-eye image is imparted with an X-direction component. Accordingly, the image detected by a photoelectric converter unit 1005L is a left-eye image mixed with a right-eye image, and the image detected by a photoelectric converter unit 1005R is a right-eye image mixed with a left-eye image. The image processing apparatus 500 performs image processing to compensate for this crosstalk phenomenon.

The ocular fundus camera system in FIG. 1A shows the principle arrangement, and its arrangement accordingly has many variations. For example, although the polarization filter unit 1002 is arranged before the objective lens 1003 in FIG. 1A, it may be arranged after the objective lens 1003.

Various embodiments of the ocular fundus camera system of the present invention will be described in detail.

<First Embodiment>

FIG. 2 shows the arrangement of an ocular fundus camera apparatus (ocular fundus camera system) according to the first embodiment.

In FIG. 2, reference numeral 700 denotes an ocular fundus camera; 600, the eye of an observation target object; and 500, an image processing apparatus. The image processing apparatus 500 performs image processing to solve the problem of shift of the polarization axis of polarized light that propagates through the ocular fundus camera. The ocular fundus camera 700 in FIG. 2 has a specific phase shifter 701 (corresponding to the equalizer unit 1001 in FIG. 1A) that solves the problem of unbalance in intensity between the two polarized light components of image light which is incident on the ocular fundus camera 700.

In the system shown in FIG. 2, the image of the fundus 600 of the observation target object is guided. The image signal of this image is processed by the image processing apparatus 500, displayed on a CRT 112, and (or) stored in a recorder 111 in the NTSC format.

Figure 6:
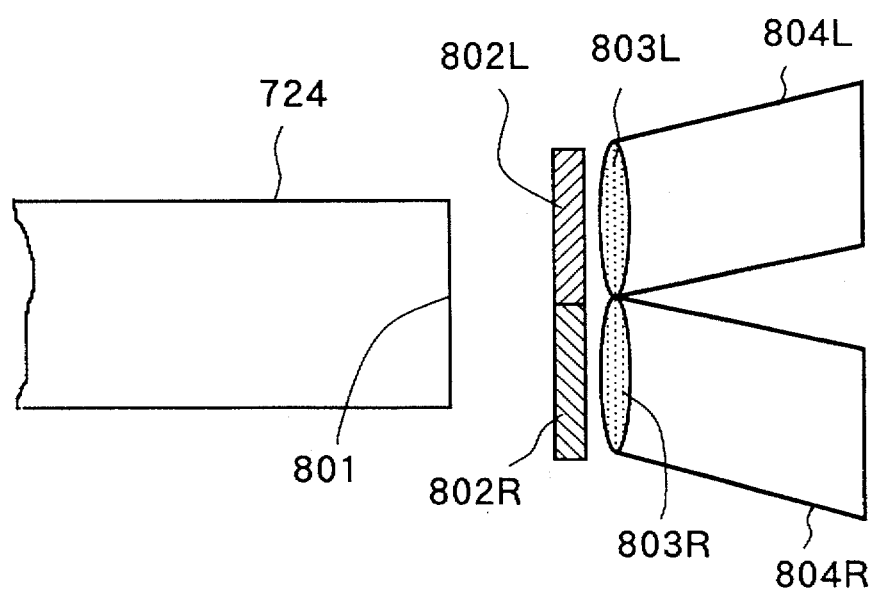
FIG. 6 shows the arrangement of the exit portion of the ocular fundus camera of the first embodiment.

An incident portion 720 is provided to one end of the ocular fundus camera 700, and an exit portion 730 is provided to the other end of the ocular fundus camera 700. The arrangement of the incident portion 720 is shown in FIGS. 3 and 4 in detail, and the arrangement of the exit portion 730 is shown in FIG. 6.

As shown in the drawings, the incident portion 720 is provided with the phase shifter 701 for correcting the intensity distribution and two polarization filters 702L and 702R for separating image light passing through the phase shifter 701 into left- and right-eye image light components. The filters 702L and 702R respectively separate light polarized in the x direction (to be referred to as an X-polarized light component hereinafter for the sake of simplicity) and light polarized in the Y direction (the Y direction is perpendicular to the X direction; to be referred as a Y-polarized light component hereinafter for the sake of simplicity), that emerge from the object 600 as the observation target, from each other, and guide them into a barrel 724. These polarized light components propagate through the barrel 724 and reach analyzers 704L and 704R of the exit portion 730. The X-polarized light component (left-eye image) and the Y-polarized light component (right-eye image) separated by the analyzers 704L and 704R are respectively converted into electrical signals by CCDs 105L and 105R (corresponding to photoelectric converter units 1005 in FIG. 1A), and then into digital image signals A' and B' by A/D converters 106L and 106R. The CCDs 105L and 105R have RGB filters (not shown). Accordingly, the digital image signals A' and B' have R, G, and B components. A separator unit 107 extracts left- and right-eye image signals L and R, generated through the filters 704L and 704R, from the digital image signals A' and B' such that they are separated from each other. A γ-correction unit 108 corrects the signals L and R so that they become suitable for the human eye.

To observe the image signals L and R on the CRT 112, these image signals are displayed on the CRT 112 through a stereoscopic image controller 113. To store the image signals L and R in the recorder 111, the signals L and R in the form of the RGB expression are converted into YIQ-system signals by a circuit 109, and then into the NTSC format by a circuit 110.

Figure 3:
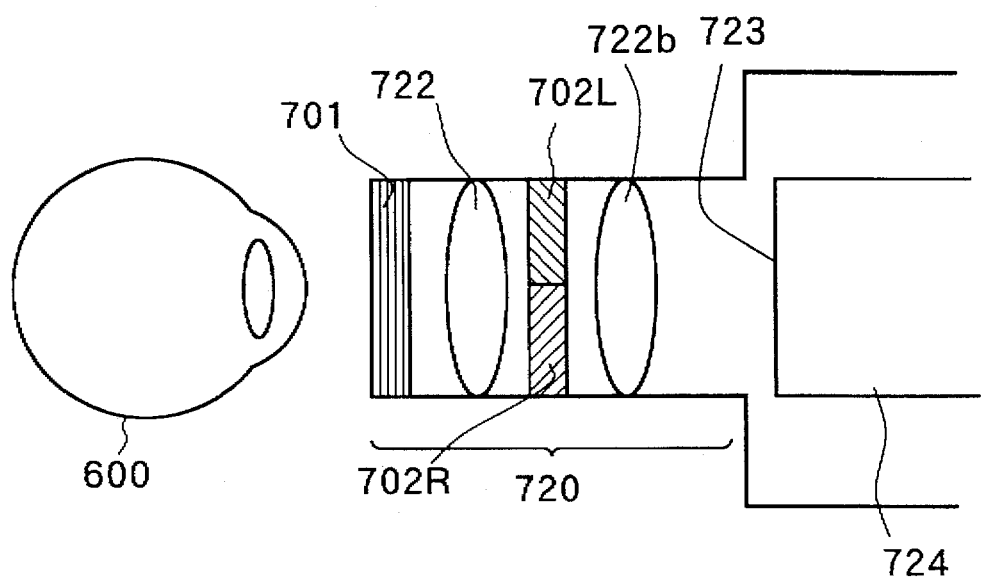
FIG. 3 is a sectional view showing the arrangement of the incident portion of the ocular fundus camera of the first embodiment.
Figure 4:
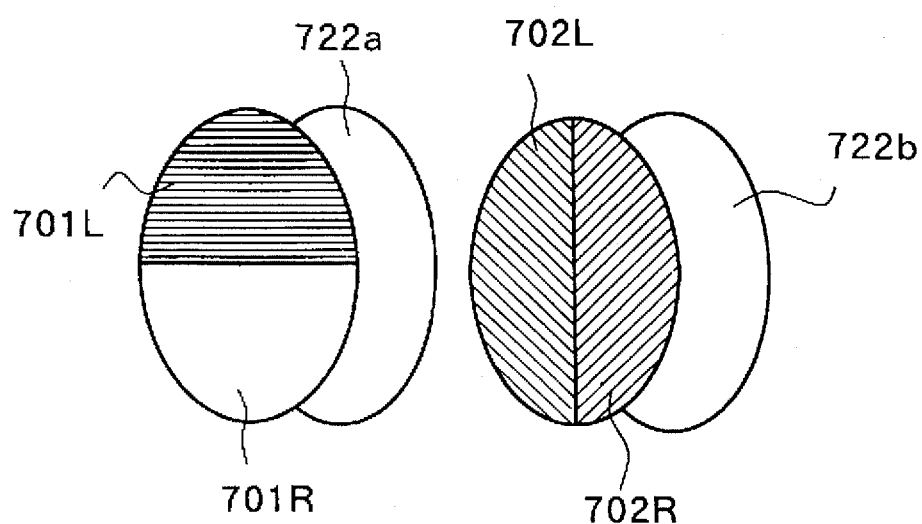
FIG. 4 shows the arrangement of an optical system at the incident portion of the ocular fundus camera of the first embodiment.

FIGS. 3 and 4 show the arrangement of the incident portion 720. In FIGS. 3 and 4, the filters 702L and 702R having two polarizing surfaces halved in a direction A and an objective lens 722a are provided behind the phase shifter 701. The objective lens 722a is provided between the phase shifter 701 and the filters 702L and 702R. An enlarging lens 722b is provided behind the filters 702L and 702R. More specifically, the pair of polarization filters 702L and 702R are sandwiched between the objective lens 722a and the enlarging lens 722b. The polarization filters 702L and 702R are located at the aperture of the objective lens 722a, i.e., at the effective center serving as the aperture in the direction of the optical axis or in its vicinity. The polarization azimuth of each of the pair of polarization filters 702L and 702R is the right angle. For the sake of descriptive convenience, the polarization azimuth of the polarization filter 702L will be referred to as the X direction, and that of the polarization filter 702R will be referred to as the Y direction. The pair of polarization filters 702L and 702R are disposed such that their horizontal planes perpendicular to the optical axis are divided into right and left regions. An incident surface 723 of the barrel 724 is provided on a surface where light emerging from the object substantially forms an image through the objective lens 722a.

In place of the lens 722, a lens unit comprising a plurality of SELFOC lenses, convex lenses, or Fresnel convex lenses may be used.

The pair of polarization filters 702L and 702R have the same areas, as described above. Accordingly, if the X-axis component of polarized light incident on the left-eye filter 702L and the Y-axis component of polarized light incident on the right-eye filter 702R are equal, the intensity of the X-polarized light component incident on the lens 722b through the filter 702L and the intensity of the Y-polarized light component incident on the GRIN lens 722b through the filter 702R must be equal to each other. As described above, however, the X- and Y-polarized light components contained in the object light emerging from the fundus 600 are not equal. The phase shifter 701 equalizes the X- and Y-polarized light components contained in the object light emerging from the fundus 600 and causes them to be incident on the pair of polarization filters 702L and 702R. In other words, the phase shifter 701 serves as an intensity equalizer.

Figure 5A:
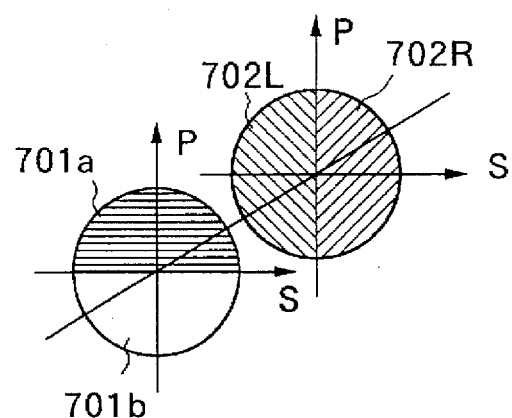
FIG. 5A shows an example of the relationship in polarizing direction between a phase shifter 701 and a polarization filter 702 of the first embodiment.

The arrangement and operation of the phase shifter 701 will be described with reference to FIG. 5A. In FIG. 5A, the phase shifter 701 has a region 701a for rotating the plane of polarization through λ/2 and a region 701b for directly transmitting light therethrough. The areas of the regions 701a and 701b of the phase shifter 701 are equal to each other. Accordingly, when arbitrarily polarized light (the polarization azimuth of which will be defined as W) is incident on the phase shifter 701 (the area and intensity of which will be defined as S and I, respectively), light emerging from the region 701a having an area of S/2 is directly incident on the polarization filter 702 with an azimuth of W+90° (with an intensity of I/2). Similarly, light emerging from the region 701b having an area of S/2 is incident on the polarization filter 702 with an azimuth of W (with an intensity of I/2). As described above, since the polarization filters 702L and 702R have polarization azimuths that are shifted from each other by 90°, even if the azimuth W is arbitrary, the light intensity of the X-direction component transmitted through the polarization filter 702L and the light intensity of the Y-direction component transmitted through the polarization filter 702R become equal to each other.

The intensities of the two polarized light components reaching the analyzers 704L and 704R are adjusted to be equal in this manner. Thus, the intensity of light (left-eye image light) passing through the filter 702L and the intensity of light (right-eye image light) passing through the filter 702R become equal to each other regardless of the polarized state of light emerging from the object 600. Therefore, the unbalance in intensity is solved by the phase shifter 701.

Figure 5B:
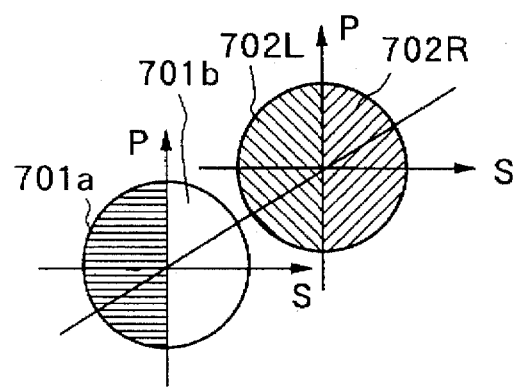
FIG. 5B shows another example of the relationship in polarizing direction between the phase shifter 701 and the polarization filter 702 of the first embodiment.
Figure 5C:
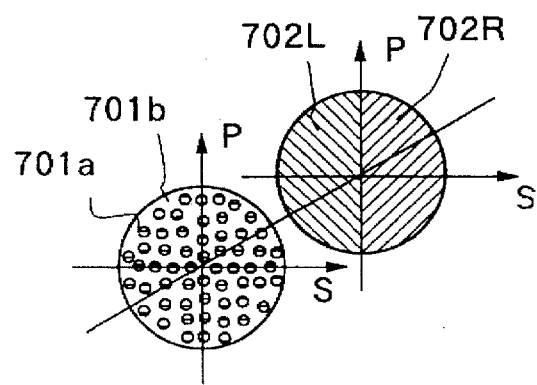
FIG. 5C shows still another example of the relationship in polarizing direction between the phase shifter 701 and the polarization filter 702 of the incident portion in FIG. 2.

FIGS. 5B and 5C show modifications of the arrangement of the phase shifter 701 shown in FIG. 5A.

More specifically, in a phase shifter 701 of the modification shown in FIG. 5B, a dividing line that divides regions 701a and 701b is set to be parallel to a dividing line that divides polarization filters 702L and 702R.

In the modification shown in FIG. 5C, a phase shifter 701 is formed to have a plurality of small phase shifter pieces 701a each having a function of shifting the polarization azimuth of transmitted light by 90° and a plurality of small transmitting pieces 701b that do not have such a function (that directly transmit light therethrough). In this case, the total area of the plurality of phase shifter pieces 701a and the total area of the plurality of transmitting pieces 701b are set to be equal to each other.

In the examples shown in FIGS. 5A to 5C, the polarization filters 702L and 702R are orthogonal. However, the present invention is not limited to these filters 702.

The phase shifter 701 shown in FIGS. 5A to 5C partially rotates the polarization azimuth of incident light. The object of the present invention can also be achieved by making the phase shifter 701 with a material that cannot maintain the polarized state of the incident light, i.e., a material that successively shifting the polarization azimuth of polarized light transmitting therethrough, in place of making the phase shifter 701 to rotate the polarization axis. More specifically, when such a material is used, the plane of polarization of light passing through the phase shifter 701 becomes non-uniform, so that the intensity of light passing through the filter 702L and the intensity of light passing through the filter 702R become equal to each other.

FIG. 6 shows the arrangement of the exit portion 730 of this ocular fundus camera.

More specifically, reference numeral 801 denotes an exit surface through which light emerges from the barrel 724; and 802L and 802R, polarization filters (corresponding to the analyzers 704 of FIG. 2). The polarization filters 802L and 802R are arranged parallel to each other so that light transmitting through the ocular fundus camera 700 is incident on them. Television cameras 804L and 804R are arranged behind the filters 802L and 802R, respectively.

With this arrangement, two polarized light components propagating through the barrel 724 are separated by the filters 802L and 802R and converted into electrical signals by the CCDs 105 (FIG. 2) through imaging lenses 803L and 803R.

The polarization azimuth of polarized light which is incident on the barrel 724 through the incident portion 720 shifts while the light propagates in the barrel 724. Due to this shift, crosstalk occurs in images observed with the right and left eyes, as described above. The image processing apparatus 500 performs image processing to prevent this crosstalk. The principle of crosstalk prevention is as follows.

Light emerging from the fundus 600 includes various polarized light components and forms an image on the polarization filter 702 through an imaging lens 722a. As described above, the filters 702L and 702R separate, of the various polarized light components, the X- and Y-polarized light components and guide them into the barrel 724. Accordingly, the left-eye image light L as the X-polarized light component and the right-eye image light R as the Y-polarized light component mixedly exist in the barrel. As the X- and Y-polarized light components are orthogonal, they can originally be separated by the analyzers 704L and 704R. In practice, however, since the polarization azimuths of the right-eye image polarized light X and left-eye image polarized light Y are set such that the right-eye image polarized light X and the left-eye image polarized light Y disperse while they are transmitted in the lens barrel, the planes of polarization wave of polarized images that are separated by the analyzers 704L and 704R do not coincide. More specifically, although the X (Y)-polarized light for the left (right)-eye image emerging from the polarization filter 702L (702R) is linearly polarized light immediately after it emerges from the polarization filter 702L (702R), its plane of polarization shifts while it propagates and becomes to have a Y (X)-polarized light component. In other words, the analyzer 704L for the left-eye image detects the X-polarized light component emerging from the polarization filter 702L and the X-polarized light component which is generated upon shift of the Y-polarized light component emerging from the polarization filter 702R and which causes crosstalk. Similarly, the analyzer 704R for the right-eye image detects the Y-polarized light component emerging from the polarization filter 702R and the Y-polarized light component which is generated upon shift of the X-polarized light component emerging from the polarization filter 702L and which causes crosstalk. As a result, a right-eye image signal is mixed in a left-eye image signal detected by the analyzer 704L, and a left-eye image signal is mixed in a right-eye image signal detected by the analyzer 704R. The separator unit 107 described above purely separates the right- and left-eye image signals from each other.

Figure 7:
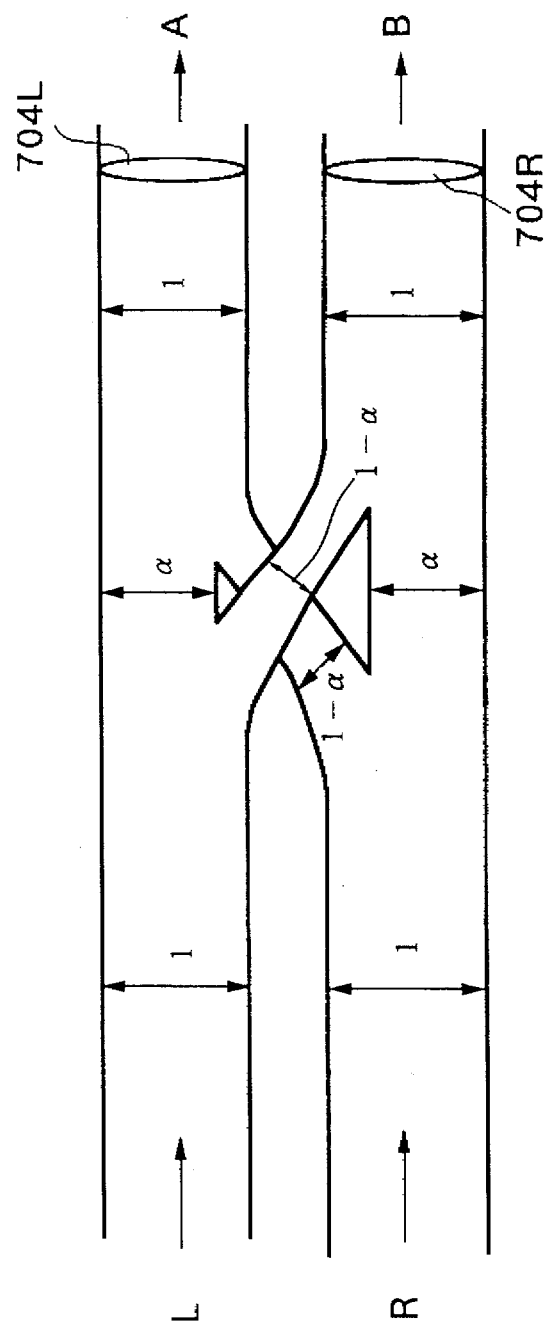
FIG. 7 is a diagram for explaining the principle of separating two polarized light components in the first embodiment.

FIG. 7 schematically shows the mixed state of light in the barrel 724. In FIG. 7, although the polarized light component L (X-polarized light component) and the polarized light component R (Y-polarized light component) are separate from each other, they actually overlap each other since both of them are waves.

A polarized light component separated by the analyzer 704L is denoted by reference symbol A, and a polarized light component separated by the analyzer 704R is denoted by reference symbol B. Under an assumption that the light behaves like particles in the optical route, if $(1-\alpha)$ % of the polarized light component L overlaps the polarized light component R and $(1-\alpha)$ % of the polarized light component R overlaps the polarized light component L, that is, if the ratio with which the barrel 724 maintains the polarized light of light passing therethrough is defined as $\alpha$, from FIG. 7, A and B are expressed as $$A = \alpha \cdot R + (1-\alpha) \cdot L \quad (1)$$

$$B = \alpha \cdot L + (1-\alpha) \cdot R \quad (2)$$

where a satisfies $0 \leq \alpha \leq 1$ and $\alpha \neq 0.5$ expresses characteristics determined by a material M, a lens count N, and the lens shape of various types of optical systems (e.g., the lens 722) used in the barrel 724.

Accordingly, from equations (1) and (2), L and R are expressed as:

$$L = \frac{A \cdot \alpha}{2\alpha - 1} - \frac{B \cdot (1-\alpha)}{2\alpha - 1} \quad (3)$$

$$R = \frac{B \cdot \alpha}{2\alpha - 1} - \frac{A \cdot (1-\alpha)}{2\alpha - 1} \quad (4)$$

Note that the polarized light components A and B are light components incident on the CCDs 105L and 105R, respectively, and the signals received by the separator unit 107 are electrical signals A' and B' output from the CCDs 105L and 105R. Generally, a linear relationship is not established between the intensity of light incident on a CCD and an output voltage of the CCD. Accordingly, the output voltages A' and B' of the A/D converters 106L and 106R cannot be directly applied in equations (3) and (4).

Figure 8:
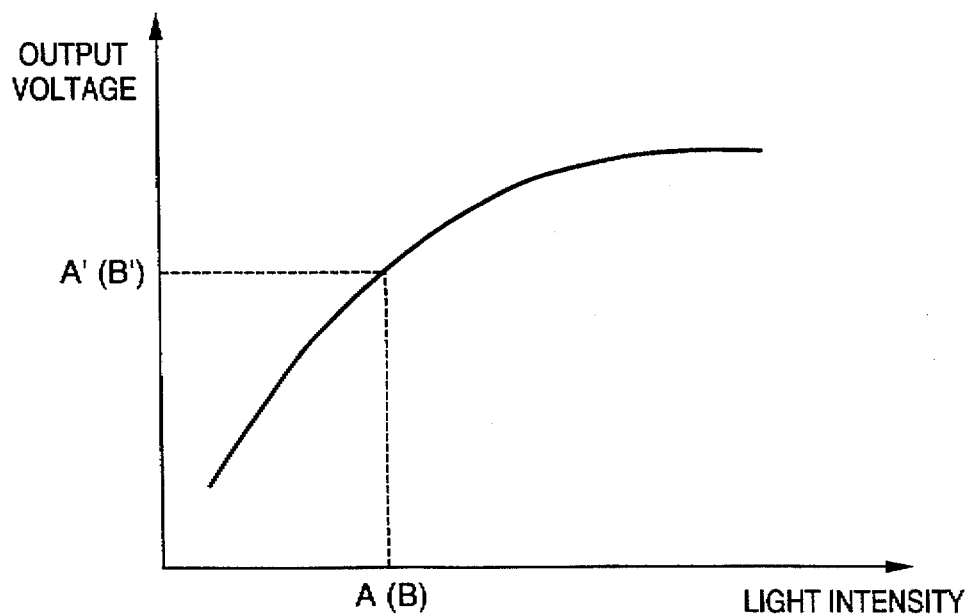
FIG. 8 is a graph for explaining the principle of photoelectric conversion of the first embodiment.

FIG. 8 shows the relationship between incident light component A to the CCD and the output voltage A' of the CCD. As this relationship is known, if the output voltages A' and B' of the CCDs 106 can be measured, the intensities of incident light components A and B to the CCDs 106 can be estimated based on the relationship of FIG. 8. The separator unit 107 quantitatively separates and extracts polarized light components L and R by applying the incident light intensities of the light components A and B to equations (3) and (4).

In practice, if the separator unit 107 is a ROM or a table that outputs the results of the arithmetic operation of equations (3) and (4), size reduction and increase in speed of the apparatus can be achieved.

Equations (1) and (2) indicate that, when a proportion is defined with which the polarized state of a bundle ($\phi$) of light which is being transmitted through the barrel is maintained by weighting of $\alpha$, this bundle can be distributed into a bundle ($\alpha\phi$) of light whose polarized state is maintained and a bundle ($1-\alpha\phi$) of light whose polarized state is not maintained. Accordingly, the arithmetic operation of proportional distribution in accordance with equations (3) and (4) is called "weighted difference".

The coefficient $\alpha$ is stored in the memory 114 shown in FIG. 2 in advance. Usually, the user inputs the material M, lens count N, lens shape, and the like of the optical system through a predetermined user interface. The controller 113 searches the recorder 111 based on the above values and reads the target $\alpha$ out from the recorder 111.

When the system has a display unit, e.g., the CRT 112, as in the system shown in FIG. 2, the user can visually observe the image sensed by the camera in the real-time manner. In this case, the user changes the value $\alpha$ by operating a dial switch 115 while observing the image on the CRT 112 so that the optimum stereoscopic images can be obtained.

In the above embodiment, stereoscopic images are received in a single optical system. However, the present invention can similarly be applied to an ocular fundus camera in which images are received by a plurality of optical systems and are transferred by one optical transfer system, as a matter of course.

As described above, according to the ocular fundus camera of the present invention, even when light to be incident itself is polarized, this polarization can be solved by equalizing the polarized states of the incident light components. Hence, the obtained left- and right-eye images are substantially equalized in intensity. Since shift of the plane of polarization of light propagating through the barrel is compensated for, occurrence of crosstalk is prevented.

The output characteristics of the CCDs 105L and 105R sometimes have linearity depending on the intensity of incident light. If the intensity of the polarized image falls within a range that guarantees the linearity of the CCDs 105, the inversion described above is not necessary.

<Second Embodiment>

Various types of ocular fundus camera systems of the present invention will be introduced by explaining an ocular fundus camera system according to the second embodiment.

Figure 9:
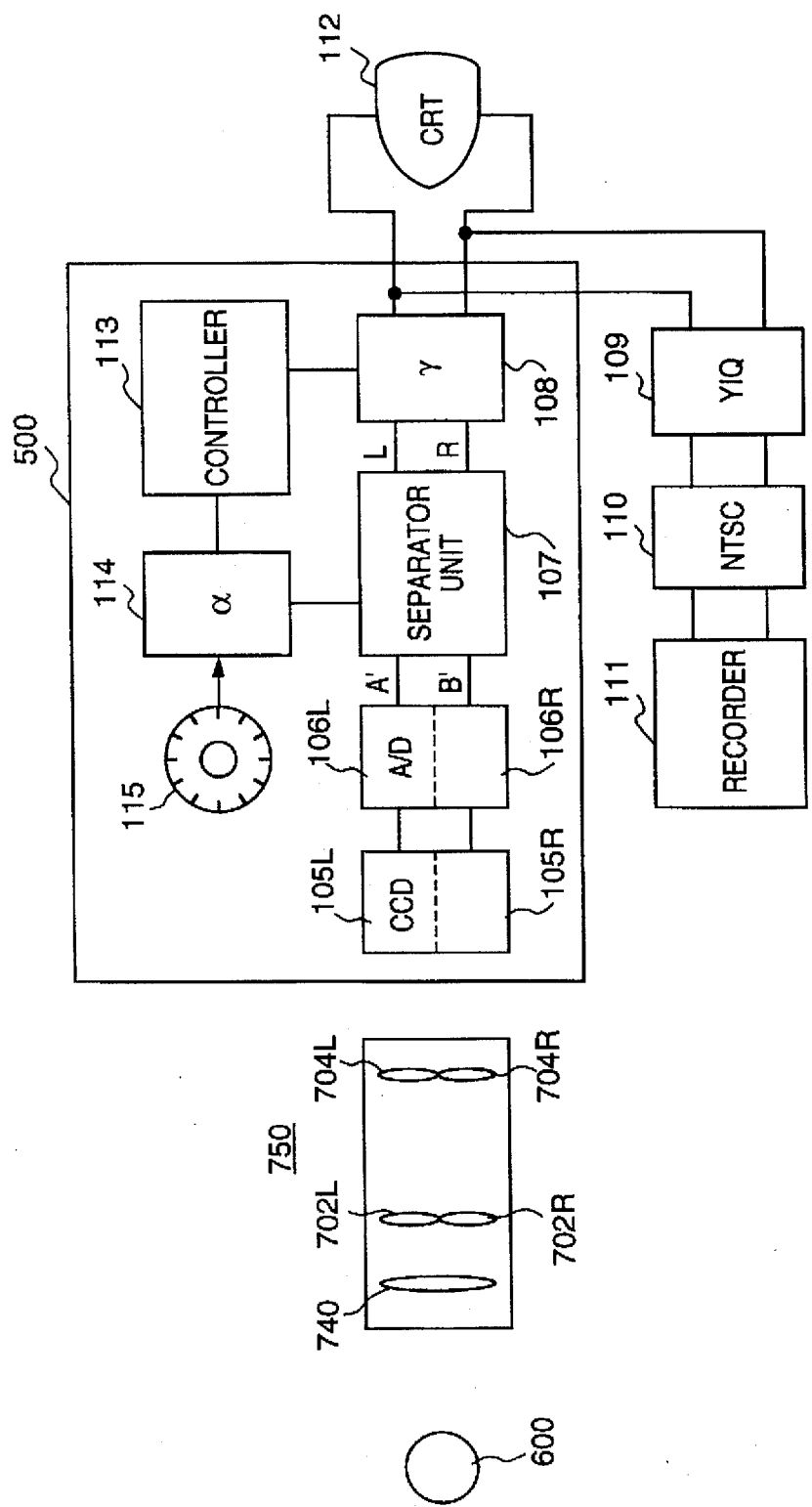
FIG. 9 shows the arrangement of an ocular fundus camera apparatus (ocular fundus camera system) according to the second embodiment of the present invention.

FIG. 9 is a schematic diagram showing the arrangement of the ocular fundus camera system according to the second embodiment. The system of the second embodiment is obtained by removing the light amount equalizer unit 1001 from the ocular fundus camera 1000 shown in FIG. 1A, thereby making the arrangement of the second embodiment simpler than the ocular fundus camera 1000 of FIG. 1A. More specifically, referring to FIG. 9, reference numeral 750 denotes an objective lens unit corresponding to the ocular fundus camera 1000 of FIG. 1A. In other words, the objective lens unit 750 has an objective lens 740, a pair of polarization filters 702, and a pair of analyzers 702 that are accommodated in a barrel (i.e., an optical route). The objective lens 740 corresponds to the objective lens 1003 of FIG. 1A.

In the system shown in FIG. 9, the image of an eye 600 is guided to an image processing apparatus 500 through the objective lens 750, displayed on a CRT 112, and (or) stored in a recorder 111 in the NTSC format.

Two polarization filters 702L and 702R are provided in addition to the lens 740 in the barrel of the objective lens unit 750, as shown in FIG. 9. The filters 702L and 702R provided in the objective lens unit 750 respectively separate light polarized in the X direction (to be referred to as an X-polarized light component hereinafter for the sake of simplicity) and light polarized in the Y direction (the Y direction is perpendicular to the X direction; to be referred as a Y-polarized light component hereinafter for the sake of simplicity), that emerge from the object 600 as the observation target, from each other. These polarized light components propagate through the barrel and reach two separate analyzers 704L and 704R. The X-polarized light component (left-eye image) and the Y-polarized light component (right-eye image) separated by the analyzers 704L and 704R are respectively converted into electrical signals by CCDs 105L and 105R, and then into digital image signals A' and B' by A/D converters 106L and 106R. The CCDs have RGB filters (not shown). Accordingly, the digital image signals A' and B' have R, G, and B components. A separator unit 107 extracts left- and right-eye image signals L and R, generated by the filters 704L and 704R, from the digital image signals A' and B' such that they are separated from each other. A γ-correction circuit 108 corrects the signals L and R so that they become suitable for the human eye.

To observe the image signals L and R on the CRT 112, these image signals are displayed on the CRT 112 through a stereoscopic image controller 113. To store the image signals L and R in the recorder 111, the signals L and R in the form of the RGB expression are converted into YIQ-system signals by a circuit 109, and then into the NTSC format by a circuit 110.

Light emerging from the fundus 600 includes various polarized light components and forms an image on the filters 702L and 702R through the imaging lens 740. As described above, the filters 702L and 702R separate, of various polarized light components, the X- and Y-polarized light components and guide them to the barrel. Accordingly, the left-eye image light component L as the X-polarized light component and the right-eye image light component R as the Y-polarized light component mixedly exist in the barrel. As the X- and Y-polarized light components are orthogonal, they can originally be separated by the analyzers 704L and 704R. In practice, however, since the polarization azimuths of the right-eye image polarized light component X and left-eye image polarized light component Y are set such that the right-eye image polarized light component X and the left-eye image polarized light component Y disperse while they are transmitted in the lens barrel, the planes of polarization wave of polarized images that are separated by the analyzers 704L and 704R do not coincide. More specifically, although the X (Y)-polarized light for the left (right)-eye image emerging from the polarization filter 702L (702R) is linearly polarized light immediately after it emerges from the polarization filter 702L (702R), its plane of polarization shifts while it propagates and becomes to have a Y (X)-polarized light component. In other words, the analyzer 704L for the left-eye image detects the X-polarized light component emerging from the polarization filter 702L and the X-polarized light component which is generated upon shift of the Y-polarized light component emerging from the polarization filter 702R and which causes crosstalk. Similarly, the analyzer 704R for the right-eye image detects the Y-polarized light component emerging from the polarization filter 702R and the Y-polarized light component which is generated upon shift of the X-polarized light component emerging from the polarization filter 702L and which causes crosstalk. As a result, a right-eye image signal is mixed in a left-eye image signal detected by the analyzer 704L, and a left-eye image signal is mixed in a right-eye image signal detected by the analyzer 704R. The separator unit 107 described above purely separates the right- and left-eye image signals from each other.

Figure 10:
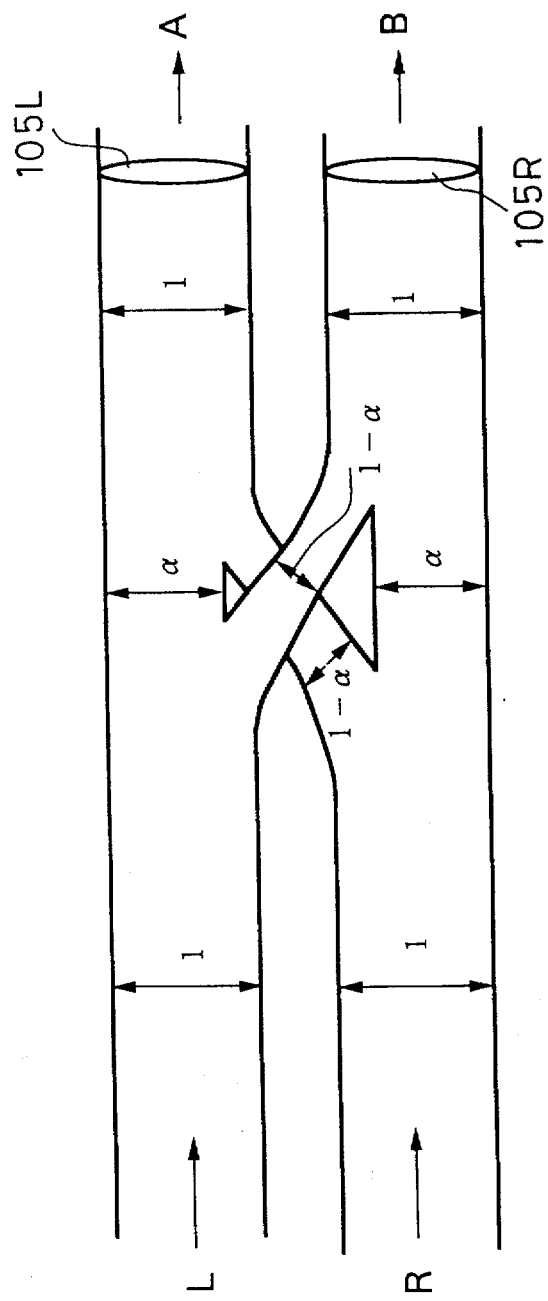
FIG. 10 is a diagram for explaining the principle of separating two polarized light components of the second embodiment.

FIG. 10 schematically shows the mixed state of light in the barrel of the objective lens unit 750. In FIG. 10, although the polarized light component L (X-polarized light component) and the polarized light component R (Y-polarized light component) are separate from each other, they actually overlap each other since both of them are waves.

Therefore, the separator unit 107 that performs image processing in accordance with equations (3) and (4) is employed in the ocular fundus camera of the second embodiment as well in the same manner as in the first embodiment, thereby preventing crosstalk.

A coefficient α is stored in a recorder 114 shown in FIG. 9 in advance. Usually, the user inputs the material M, lens count N, lens shape, and the like of the optical system through a predetermined user interface. The controller 113 searches the recorder 114 based on the above values and reads the target α from the recorder 114.

When the system has a display unit, e.g., the CRT 112, as in the system shown in FIG. 9, the user can visually observe the image sensed by the ocular fundus camera in the real-time manner. In this case, the user changes the value α by operating a dial switch 115 while observing the image on the CRT 112 so that the optimum stereoscopic images can be obtained.

The output characteristics of the CCDs 105L and 105R sometimes have linearity depending on the intensity of incident light. If the intensity of the polarized image falls within a range that guarantees the linearity of the CCDs 105, the inversion described above is not necessary.

The practical arrangement of the ocular fundus camera of the second embodiment will be described in more detail.

Figure 11:
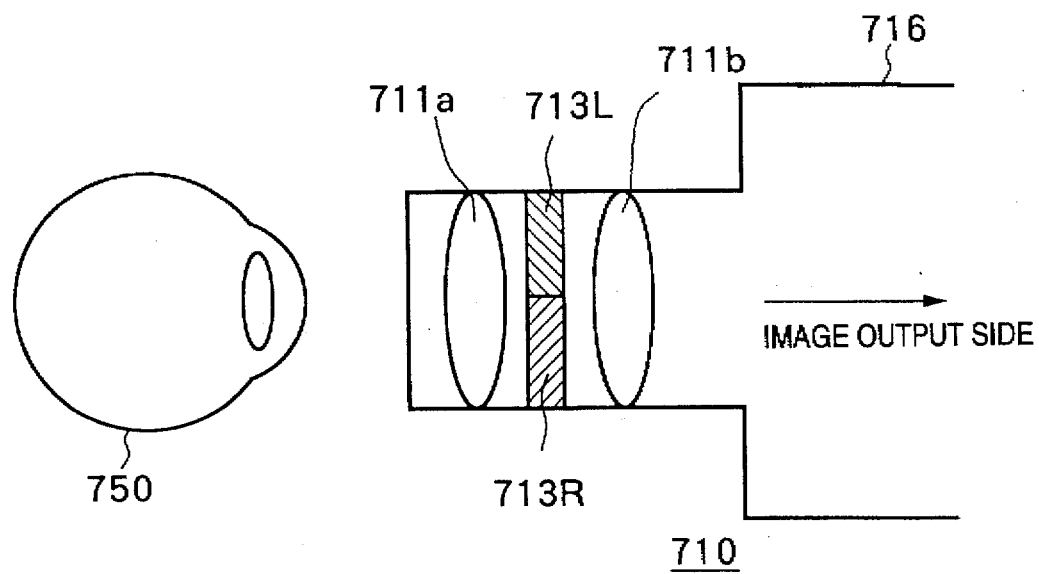
FIG. 11 is a sectional view showing an example of the arrangement of an objective lens unit for an ocular fundus camera used in the ocular fundus camera system of the second embodiment.
Figure 12:
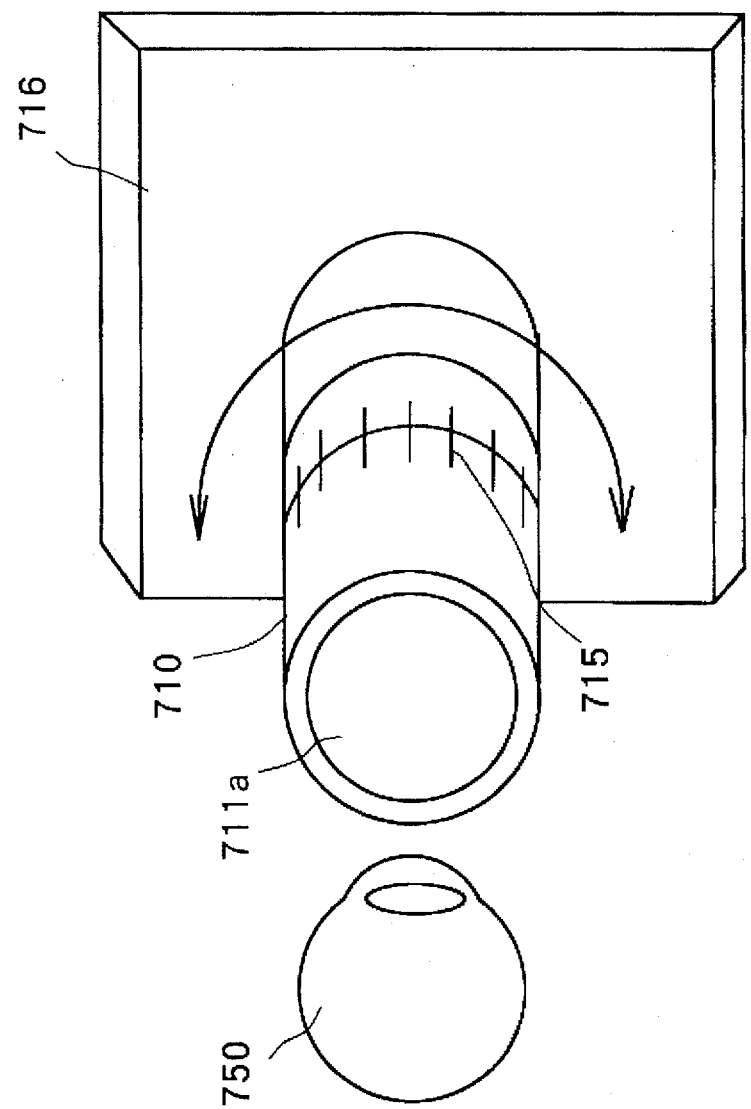
FIG. 12 is a perspective view showing an example of the arrangement of the objective lens unit for the ocular fundus camera of the second embodiment.

FIG. 11 is a sectional view showing the arrangement of an objective lens unit 710 as a practical example of the objective lens unit 750 of the stereoscopic ocular fundus camera shown in FIG. 9, and FIG. 12 is a perspective view of the objective lens unit 710.

The objective lens unit 710 is fixed with a stand 716. Lenses 711a and 711b are provided in the barrel of the objective lens unit 710. These lenses 711a and 711b correspond to the lens 740 in FIG. 9. Two polarization filters 713L and 713R are provided side by side between the lenses 711a and 711b, as shown in FIG. 11. The filters 713 correspond to the filters 702 in FIG. 9. The positions of the filters 713 in the optical axis are set at the effective center serving as the aperture of the objective lens 711a in the direction of the optical axis, or in its vicinity. The polarization azimuths of the two filters 713L and 713R are orthogonal, and will be defined as X and Y directions, respectively, for the sake of descriptive convenience. A plane that divides the polarization filters 713L and 713R is perpendicular to the optical axis of the lens 711 and includes this optical axis. Accordingly, light components that pass through the polarization filters 713L and 713R are respectively X- and Y-polarized light components. More specifically, the optical images of the X- and Y-polarized light components respectively passing through the polarization filters 713L and 713R are formed on a predetermined interface on the image output side. Thus, a parallax image existing in the effective aperture of the objective lens unit 710 can be converted into two polarized images, and the two polarized images can be transferred to the image output side through one optical system (711) in the housing of the ocular fundus camera.

Figure 13:
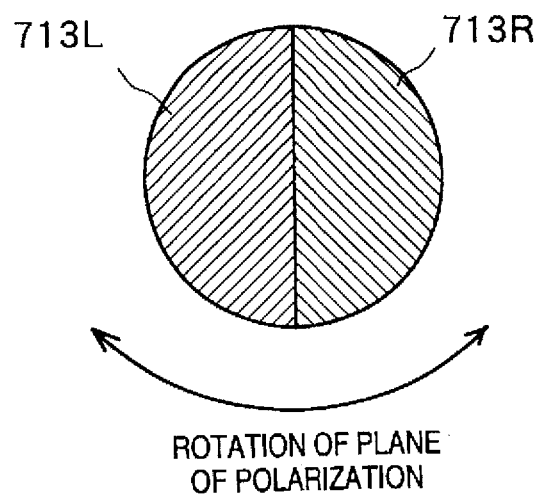
FIG. 13 shows the arrangement of polarization filters in the objective lens unit of the second embodiment.
Figure 14:
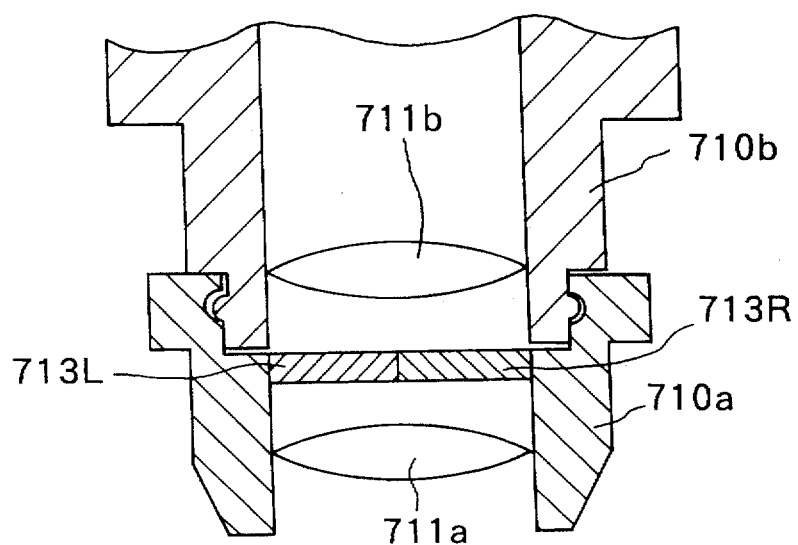
FIG. 14 is a sectional view showing the arrangement of the objective lens unit in FIG. 11.

FIG. 14 is a sectional view showing the internal arrangement of the objective lens unit 710. The barrel of the objective lens unit 710 is divided into an outer barrel 710a and an inner barrel 710b. The lens 711a and the polarization filters 713L and 713R are held by the barrel 710a, and the lens 711b is held by the barrel 710a. The barrel 710b can be rotated relative to the barrel 710a about its optical axis as the center. Accordingly, as shown in FIG. 13, the polarization filters 713L and 713R are pivotal about the optical axis as the center. More specifically, when the barrel 710b is held and rotated, the planes of polarization of the polarization filters 713L and 713R are rotated.

The barrels 710a and 710b of the objective lens unit 710 are formed with scales 715 (FIG. 12). From these scales 715, the user can confirm the number of turns through which the planes of polarization have been rotated.

The lens portion 711 may employ an ordinary convex lens, a Fresnel convex lens, or a plurality of lenses. The positions, sizes, and shapes of the lens portion 711 and the polarization filters 713 are arbitrary as far as they are within the spirit and scope of the present invention.

Although the polarization azimuths of the polarization filters 713 are preferably the right angle, they are not particularly limited as far as they are different from each other.

Figure 15:
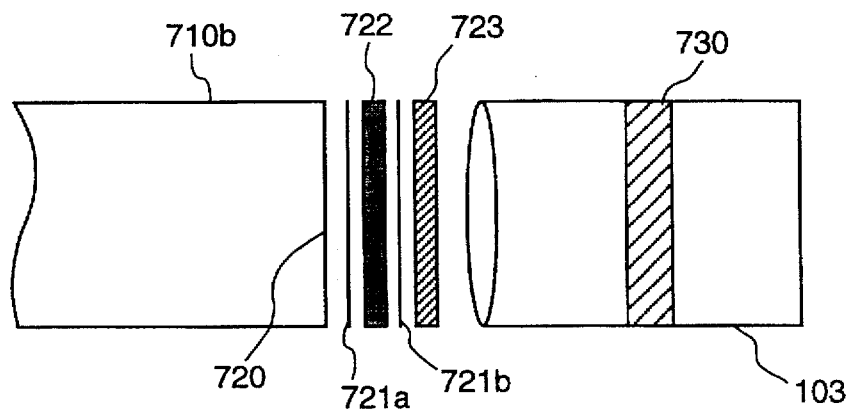
FIG. 15 is a sectional view showing an example of the arrangement of the image output side of the ocular fundus camera of the second embodiment.

FIG. 15 is a sectional view showing the arrangement of the light exit side of the objective lens unit 710 of the second embodiment in FIG. 9. As shown in FIGS. 9 and 11, the objective lens unit 710 guides two polarized light components whose polarization azimuths are orthogonal into the barrel.

In FIG. 15, reference numeral 720 denotes an exit surface of image light in the barrel 710b. Transparent electrodes 721a and 721b are provided behind the exit surface 720, and a liquid crystal device 722 is sandwiched between the transparent electrodes 721a and 721b. An analyzer 723 is provided behind the electrode 721b.

The polarization azimuth of the liquid crystal device 722 can be changed by controlling the voltage applied to the transparent electrodes 721a and 721b. More specifically, the liquid crystal device 722, the transparent electrodes 721a and 721b, and the polarization filter 723 serving as the analyzer serve as a "light valve" that transmits only the X-polarized light component upon application of the first predetermined voltage to the electrodes and only the Y-polarized light component upon application of the second predetermined voltage different from the first voltage. Accordingly, the liquid crystal device 722, the transparent electrodes 721a and 721b, and the polarization filter 723 serving as the analyzer correspond to the analyzers 704L and 704R in FIG. 9.

Figure 16:
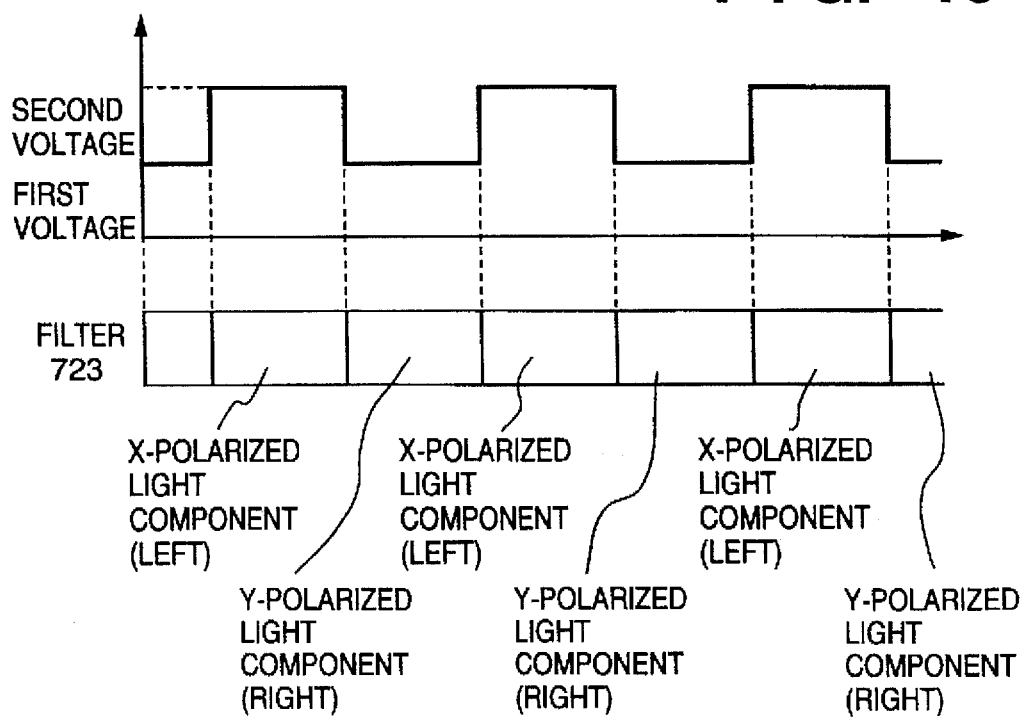
FIG. 16 is a timing chart of the control signal for the ocular fundus camera in FIG. 15.

FIG. 16 shows the relationship among the timings of the first and second voltages described above and the timing of output light emerging from the polarization filter 723. More specifically, when the first and second voltages as signals output from the stereoscopic image controller 113 (FIG. 9) are controlled, X-polarized light component (left-eye image light component) and Y-polarized light component (right-eye image light component) are sequentially output from the filter 723 in the time-interlace manner.

In the ocular fundus camera of this embodiment, since the time-interlace scheme is employed as described above, two CCDs (FIG. 9) are not required, and one CCD 105 suffices, as shown in FIG. 8. Referring to FIG. 15, reference numeral 730 denotes a television camera having in it the CCD 105 that forms an optical image. Then, the CCD 105 alternately outputs two image signals A' and B' in synchronism with sync signals.

The separator unit 107 extracts the separated image signals L and R based on these image signals A' and B', as described above.

When the ocular fundus camera of this embodiment is used, left- and right-eye images are alternately generated, as shown in FIG. 16. If the left- and right-eye images are alternately displayed on the CRT 112 in the time-interlace manner, flicker occurs. When the time-interlace left- and right-eye images are recorded in the recorder 111, the recording efficiency is degraded. Hence, to convert image signals obtained by using the camera in FIG. 15 into parallel image signals, a known synchronizing unit may be used. In this case, conversion of time-interlace signals into time-parallel signals may be performed before "weighted difference" processing.

Figure 17:
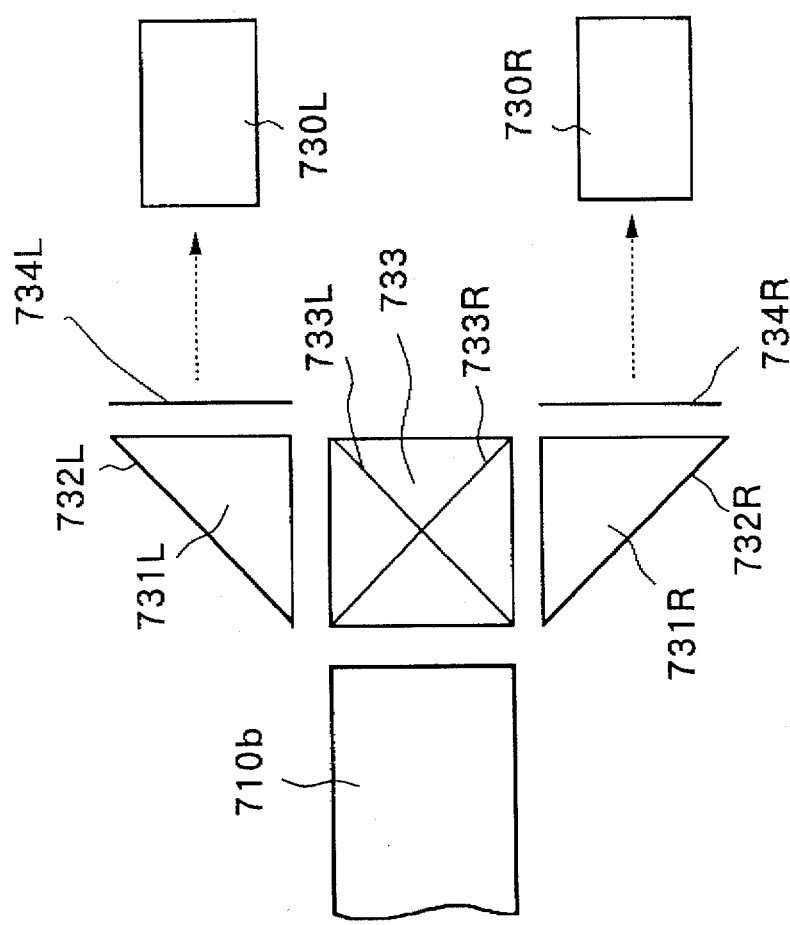
FIG. 17 shows the arrangement of a modification of the ocular fundus camera in FIG. 15.

FIG. 17 shows the arrangement of a modification of the example of the FIG. 15 of the light exit side of the ocular fundus camera of the second embodiment.

Referring to FIG. 17, reference numeral 733 denotes a beam splitter; 731L and 731R, prisms; 732L and 732R, reflecting surfaces formed on the respective prisms; 734L and 734R, analyzers; and 730L and 730R, television cameras. The beam splitter 733 is constituted by adhering four prisms, and has two reflecting surfaces 733L and 733R.

More specifically, two polarized images passing through the barrel 710b are divided into two optical paths by the beam splitter 733. Light of each optical path includes two polarized images. The light components of two systems each including the two polarized images are respectively incident on the prisms 731L and 731R, are reflected by the reflecting surfaces 732L and 732R, and are incident on the polarization filters 734L and 734R. The polarization filters 734L and 734R are set in advance such that they transmit, of the two polarized light components, only the X- and Y-polarized light components, respectively.

Accordingly, the camera 730L senses the left-eye image including the X-polarized light component, and the camera 730R senses the right-eye image including the Y-polarized light component. The images sensed by the cameras 730L and 730R are input to the image processing apparatus shown in FIG. 9, and are subjected to the weighted difference processing described above. Due to this weighted difference processing, even if a light component which has been the Y (X)-polarized light component in the objective lens unit 710 is included in the X (Y)-polarized light component separated by the filter 734L (734R), the separator unit 107 extracts the left-eye image (X-polarized light component) detected by the objective lens unit 710 and the right-eye image (Y-polarized light component) detected by the objective lens unit 710, as described above.

In this manner, a pair of stereoscopic images in which the right- and left-eye images are completely separated from each other can be obtained with the ocular fundus camera shown in FIG. 17 as well.

When the beam splitter 733 can select polarization of two polarized images, the polarization filters 734L and 734R are not necessary.

In FIG. 17, the beam splitter 733 having two reflecting surfaces and prisms each having one reflecting surface are provided so that exit light is collimated. In some cases, however, one optical path may be perpendicular to the other. In this case, an ordinary beam splitter (that transmits the X-polarized light component and reflects the Y-polarized light component) may be used.

In the second embodiment described above, stereoscopic images are received in a single optical system. However, this embodiment can similarly be applied to an ocular fundus camera in which images are received by a plurality of optical systems and are transferred by one optical transfer system, as a matter of course.

As described above, in the image processing apparatus of the camera system, the ocular fundus camera, the method of controlling the ocular fundus camera according to the second embodiment, two high-precision image data can be obtained from images that are obtained by one light optical member (e.g., a lens) which transfers two polarized images having a parallax, by employing proportional distribution (weighted difference processing). In other words, this proportional distribution (weighted difference processing) in the second embodiment enables use of an inexpensive ocular fundus camera.

When the coefficient (α) for the proportional distribution (weighted difference processing) is determined or stored in advance, the operability of the ocular fundus camera can be improved.

Image processing of the second embodiment enables use of ocular fundus cameras having various arrangements.

The objective adapter of the second embodiment is suitable for the above ocular fundus camera and can adjust the angle of the plane of polarization.

<Third Embodiment>

The ocular fundus cameras of the third embodiment (FIGS. 18, 19, and 20) are obtained by modifying an eyepiece unit 780 of the ocular fundus camera of the second embodiment.

Figure 18:
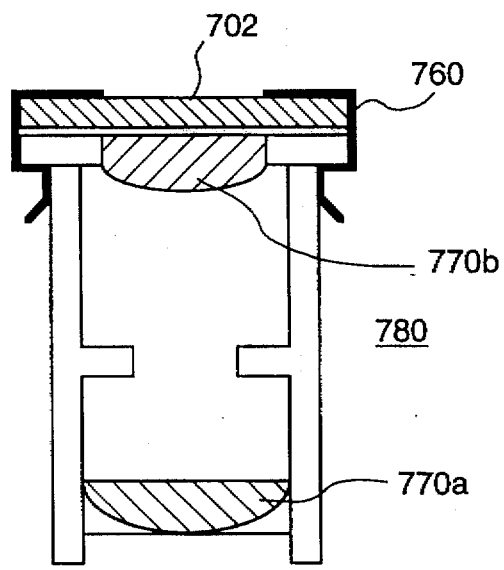
FIG. 18 shows the arrangement of the eyepiece unit of an ocular fundus camera according to the third embodiment.

More specifically, the characteristic feature of the eyepiece unit 780 of the third embodiment in FIG. 18 resides in that a polarization filter 702 is arranged close to an eyepiece 770b by using a retainer 760. The polarization filter 702 consists of two regions, i.e., a region for transmitting only the X-polarized light component and a region for transmitting only the Y-polarized light component, in the same manner as in the first embodiment.

Figure 19:
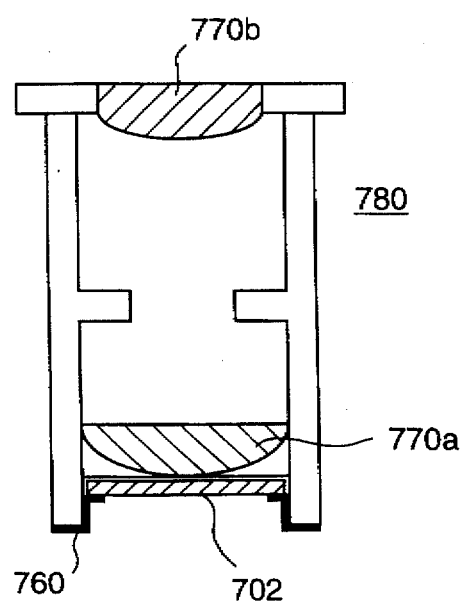
FIG. 19 shows another arrangement of the eyepiece unit of the ocular fundus camera of the third embodiment.

FIG. 19 shows the first modification of the third embodiment. The characteristic feature of the first modification resides in that a polarization filter 702 is arranged close to an objective lens 770a.

Figure 20:
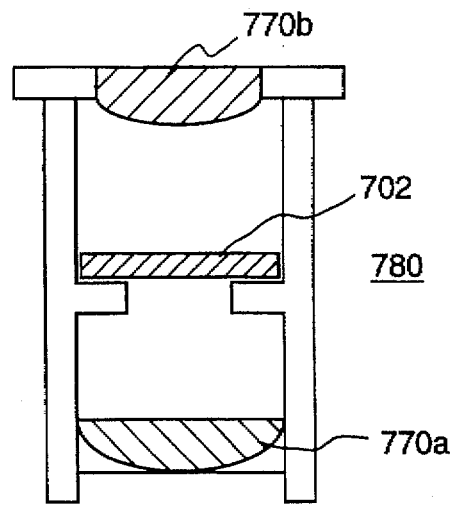
FIG. 20 shows still another arrangement of the eyepiece unit of the ocular fundus camera of the third embodiment.

FIG. 20 shows the second modification of the third embodiment. The characteristic feature of the second modification resides in that a polarization filter 702 is provided between an objective lens 770a and an eyepiece 770b.

<Fourth Embodiment>

In the ocular fundus camera system of the first embodiment, both the scheme of equalizing the light intensities and image processing for preventing crosstalk caused by shift of the plane of polarization are employed. The second embodiment provides an ocular fundus camera system which employs only image processing for preventing crosstalk caused by shift of the plane of polarization. In both systems of the first and second embodiments, the image of a target object is displayed on a CRT display or is recorded in a recorder. The fourth embodiment which will be described hereinafter provides an ocular fundus camera that allows the observer to directly observe, with his eyes, an image which is obtained from image light emerging from the observation target and which is not subjected to image processing described above. More specifically, both in the first and second embodiments, image light is photoelectrically converted and then converted into RGB image data, thereby obtaining a visual image. In contrast to this, with the ocular fundus camera of the fourth embodiment, image light emerging from an objective lens unit 700 can be directly seen with the observer's eyes. For this reason, the system of the fourth embodiment does not perform image processing and thus does not have a function of preventing crosstalk caused by shift of the plane of polarization. As far as the number of optical systems used in the optical path of the ocular fundus camera is decreased or shift of the plane of polarization is prevented, only equalization of the light intensities need be performed, which is the first function, and no problem occurs in practice.

Figure 21:
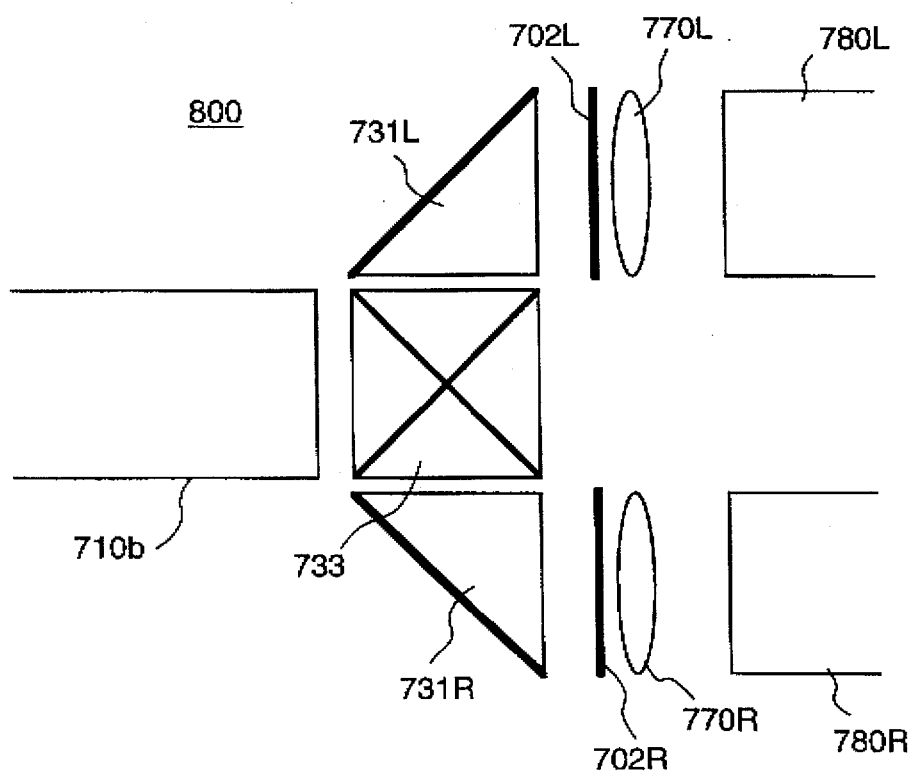
FIG. 21 shows the arrangement of the eyepiece unit of an ocular fundus camera according to the fourth embodiment.

The characteristic feature of the fourth embodiment resides in that an eyepiece unit 800 shown in FIG. 21 is used. In the eyepiece unit 800 shown in FIG. 21, light in which X- and Y-polarized light components overlap is separated into two optical paths by using optical prisms 733, 731L, and 731R, and one optical path is guided to a (left-eye) polarization filter 702L while the other optical path is guided to a (right-eye) polarization filter 702R. A left-eye eyepiece 770L is provided behind the filter 702L, and a right-eye eyepiece 770R is provided behind the filter 702R. Reference numeral 780 denote television cameras.

In the fourth embodiment, since the polarization filters 702 are provided on the eyepiece side in this manner, a unit obtained by removing the filter 702 from the objective lens unit 750 (FIG. 9) of the first embodiment can be used as the objective lens unit of the fourth embodiment.

<Fifth Embodiment>

Figure 22:
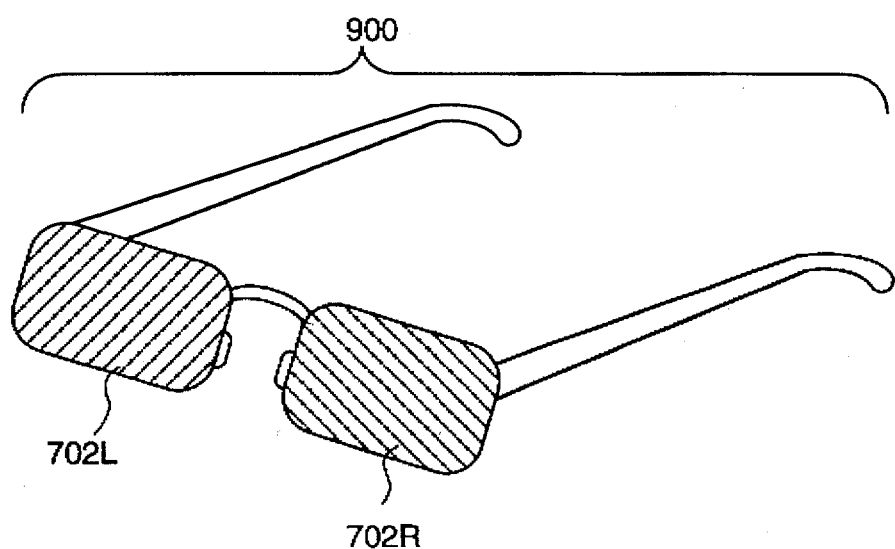
FIG. 22 shows the arrangement of glasses used in an eyepiece unit according to the fifth embodiment.

FIG. 22 shows glasses which are worn by the observer who uses an ocular fundus camera of the fifth embodiment. Polarization filters 702L and 702R are respectively mounted on the lenses of glasses 900 shown in FIG. 22. These glasses 900 have polarization filters for separating right- and left-eye images from each other. Hence, as the eyepiece unit of the ocular fundus camera apparatus using the glasses 900, a modification of the eyepiece unit of the fourth embodiment can be employed, i.e., one obtained by removing the filters 702L and 702R from the eyepiece unit 800 shown in FIG. 21 can be employed. As the objective lens unit, one obtained by removing the polarization filters from the objective lens unit of the first embodiment is employed.

In all the embodiments described above, stereoscopic images are received in a single optical system. However, the present invention can similarly be applied to an ocular fundus camera in which images are received by a plurality of optical systems and are transferred by one optical transfer system, as a matter of course.

As many apparently widely different embodiments of the present invention can be made without departing from the spirit and scope thereof, it is to be understood that the invention is not limited to the specific embodiments thereof except as defined in the appended claims.

What is claimed is:

1. An image processing apparatus for an ocular fundus camera having an optical system that transfers first and second image light components which have a parallax therebetween and which can be separated from each other, comprising:
   converting means for converting the first and second image light components into first and second image signals; and
   generating means for generating first and second image data by performing proportional distribution of the first and second image signals in accordance with a predetermined coefficient.

2. The apparatus according to claim 1, wherein the predetermined coefficient has values ranging from 0 to 1, and further comprising adjusting means, allowing a user to operate, for adjusting the coefficient.

3. The apparatus according to claim 1, wherein
   said converting means has an image sensing element for converting the first and second image light components into the first and second image signals as electrical signals, and
   said generating means has inverting means for inverting the first and second image signals sent from said image sensing element into first and second light intensity data representing light intensities, and means for performing proportional distribution of the light intensity data in accordance with the predetermined coefficient.

4. The apparatus according to claim 1, wherein the first and second image light components in said optical system are polarized substantially differently from each other.

5. The apparatus according to claim 1, further comprising means for storing or displaying the first and second image data.

6. The apparatus according to claim 1, wherein the predetermined coefficient is determined in advance based on a material, count, and shape of a lens provided to said optical system.

7. The apparatus according to claim 6, further comprising means for inputting the material, shape, and count of said lens.

8. An ocular fundus camera apparatus comprising:
   an ocular fundus camera having an optical system that transfers first and second image light components which have a parallax therebetween and which can be separated from each other;
   converting means for converting the first and second image light components into first and second image signals; and
   generating means for generating first and second image data by performing proportional distribution of the first and second image signals in accordance with a predetermined coefficient.

9. The apparatus according to claim 8, wherein the predetermined coefficient has values ranging from 0 to 1, and
   further comprising adjusting means, allowing a user to operate, for adjusting the coefficient.

10. The apparatus according to claim 8, wherein
    said converting means has an image sensing element for converting the first and second image light components into the first and second image signals as electrical signals, and
    said generating means has inverting means for inverting the first and second image signals sent from said image sensing element into first and second light intensity data representing light intensities, and means for performing proportional distribution of the light intensity data in accordance with the predetermined coefficient.

11. The apparatus according to claim 8, further comprising means for storing or displaying the first and second image data.

12. The apparatus according to claim 8, further comprising a marker, provided in an optical path, for indicating a direction of a dividing line that halves said polarization filters.

13. The apparatus according to claim 8, wherein the predetermined coefficient is determined in advance based on a material, count, and shape of a lens provided to said optical system.

14. The apparatus according to claim 13, further comprising means for inputting the material, shape, and count of said lens.

15. The apparatus according to claim 8, wherein the first and second image light components in said optical system are polarized substantially differently from each other.

16. The apparatus according to claim 15, wherein
    said optical system of said ocular fundus camera has an incident portion provided to a distal end side of said ocular fundus camera, and an exit portion provided to a proximal end side of said ocular fundus camera, and
    said exit portion has polarization axis rotating means for rotating polarization axes of two polarized images passing through said ocular fundus camera in a time-interlace manner, and an analyzer provided behind said rotating means.

17. The apparatus according to claim 13, wherein
    said optical system of said ocular fundus camera has an incident portion provided to a distal end side of said ocular fundus camera, and an exit portion provided to a proximal end side of said ocular fundus camera, and
    said exit portion has a beam splitter for separating optical paths of two polarized images passing through said ocular fundus camera, and a pair of polarization filters respectively passing the separated polarized images therethrough and having polarization azimuths different from each other.

18. The apparatus according to claim 15, further comprising equalizing means, provided in front of said pair of polarization filters, for equalizing two polarized light components of incident light.

19. The apparatus according to claim 15, wherein
    said optical system of said ocular fundus camera has an incident portion provided to a distal end side of said ocular fundus camera, and an exit portion provided to a proximal end side of said ocular fundus camera, and
    said incident portion has a pair of polarization filters which are provided at an effective center serving as an aperture in a direction of an optical axis or in a vicinity thereof, which have different polarization azimuths, and which are divisionally disposed on right and left regions of a plane substantially perpendicular to the optical axis.

20. The apparatus according to claim 19, wherein said pair of polarization filters respectively have semicircular shapes.

21. A method of controlling an ocular fundus camera having an optical system that transfers first and second image light components which have a parallax therebetween and which can be separated from each other, comprising the steps of:

converting the first and second image light components into first and second image signals by controlling an image sensing element; and generating first and second image data by performing proportional distribution of the first and second image signals based on conversion characteristics of said image sensing element and a predetermined coefficient.

22. The method according to claim 21, wherein the predetermined coefficient is stored as a value corresponding to a geometric shape of said optical system.

23. An objective adapter of an ocular fundus camera having an objective lens in a barrel thereof, comprising:

a pair of polarization filters arranged side by side at an effective center serving as an aperture of said objective lens in a direction of a plane perpendicular to an optical axis of said barrel; and means for rotating said pair of polarization filters about the optical axis in said barrel as a center.

24. The adapter according to claim 23, wherein said barrel has a first barrel portion for supporting at least said pair of polarization filters and a second barrel portion for supporting a remaining portion of said adapter, said first barrel portion being supported to be pivotal with respect to said second barrel portion, and at least one of said first and second barrel portions is formed with a scale for aiding visual observation of a pivot amount of said first barrel portion.

25. The adapter according to claim 23, wherein said pair of polarization filters have semicircular shapes and substantially form a circle when fitted with each other.

26. An ocular fundus camera for separating image light incident through an observation lens into two polarization images, propagating the two polarization images through one optical system, and using the two polarized images as two parallax images, comprising:

equalizing means for equalizing two polarized light components of incident light; and optical means provided at rear of said equalizing means for separating the polarized images having two equalized polarized light components, whereby intensities of the two parallax images obtained by said optical means become equal.

27. The ocular fundus camera according to claim 26, wherein said equalizing means solves polarization characteristics of the incident light.

28. The ocular fundus camera according to claim 26, wherein said equalizing means has means for rotating a polarization angle of the incident light.

29. The ocular fundus camera according to claim 28, wherein said equalizing means comprises a plurality of phase shifter pieces, each piece shifting a phase of transmitting light, and a plurality of light-transmitting plate pieces, each piece transmitting light without shift, wherein an entire area of said plurality of phase shifter pieces is substantially same as that of said plurality of light-transmitting plate pieces, wherein said optical means comprises a pair of polarization filters having polarization azimuth different from each other and having a same area, and wherein light which is phase-shifted by said plurality of phase shifter pieces and light which passes said plurality of light-transmitting plate pieces are incident on said pair of polarization filters.

30. The ocular fundus camera according to claim 28, wherein said equalizing means comprises a phase shifter which alters a phase of transmitting light and a light-transmitting plate which does not alter a phase of the transmitting light, an area of said phase shifter is a same as that of said of said light-transmitting plate, and said optical means comprises a pair of polarization filters having polarization azimuth different from each other and having a same area, and wherein light which is phase-shifted by said phase shifter and light which passes said light-transmitting plate are incident on said pair of polarization filters.

31. The ocular fundus camera according to claim 30, said phase shifter shifts a phase of transmitting light by $\lambda/2$.

32. The ocular fundus camera according to claim 30, each phase shifter piece shifts a phase of transmitting light by $\lambda/2$.

33. The ocular fundus camera according to claim 30, wherein a primary surface of said pair of polarization filters is perpendicular to an optical axis of the ocular fundus camera, and a primary surface of said phase shifter and light-transmitting plate is perpendicular to the optical axis of the ocular fundus camera.

34. The ocular fundus camera according to claim 33, wherein said primary surfaces of the pair of polarization filters are substantially semicircular, and are flush with each other to make a circle, and said primary surfaces of the said phase shifter and light-transmitting plate are substantially semicircular, and are flush with each other to make a circle.

35. The ocular fundus camera according to claim 34, wherein a first line which separates one of said pair of polarization filters from the other of said pair of polarization filters is perpendicular to a line which separates said phase shifter from said light-transmitting plate.

36. The ocular fundus camera according to claim 34, wherein a first line which separates one of said pair of polarization filters from the other of said pair of polarization filters is parallel to a line which separates said phase shifter from said light-transmitting plate.

* * * * *